United States Patent
Lorenceau et al.

(10) Patent No.: US 12,256,992 B2
(45) Date of Patent: Mar. 25, 2025

(54) OCULAR OBSERVATION DEVICE

(71) Applicants: SORBONNE UNIVERSITE, Paris (FR); CENTRE NATIONAL DE LA RECHERCHE SCIENTIFIQUE—CNRS, Paris (FR); INSERM (INSTITUT NATIONAL DE LA SANTÉ ET DE LA RECHERCHE MÉDICALE), Paris (FR)

(72) Inventors: Jean Lorenceau, Paris (FR); Suzon Ajasse, Rosny sous Bois (FR)

(73) Assignees: SORBONNE UNIVERSITE, Paris (FR); CENTRE NATIONAL DE LA RECHERCHE SCIENTIFIQUE—CNRS, Paris (FR); INSERM (INSTITUT NATIONAL DE LA SANTÉ ET DE LA RECHERCHE MÉDICALE), Paris (FR)

( * ) Notice: Subject to any disclaimer, the term of this patent is extended or adjusted under 35 U.S.C. 154(b) by 851 days.

(21) Appl. No.: 17/261,687

(22) PCT Filed: Jul. 16, 2019

(86) PCT No.: PCT/FR2019/051778
§ 371 (c)(1),
(2) Date: Jan. 20, 2021

(87) PCT Pub. No.: WO2020/016517
PCT Pub. Date: Jan. 23, 2020

(65) Prior Publication Data
US 2021/0259543 A1    Aug. 26, 2021

(30) Foreign Application Priority Data
Jul. 20, 2018 (FR) ..................... 18 56737

(51) Int. Cl.
*A61B 3/11* (2006.01)
*A61B 3/00* (2006.01)
*A61B 3/024* (2006.01)

(52) U.S. Cl.
CPC ............ *A61B 3/112* (2013.01); *A61B 3/0008* (2013.01); *A61B 3/0041* (2013.01); *A61B 3/024* (2013.01)

(58) Field of Classification Search
CPC ....... A61B 3/112; A61B 3/113; A61B 3/0091; A61B 3/0008; A61B 3/024; A61B 5/163;
(Continued)

(56) References Cited

U.S. PATENT DOCUMENTS

2010/0085339 A1  4/2010  Harada et al.
2011/0292342 A1* 12/2011 Maddess .................. A61B 5/40
                                                                351/209

FOREIGN PATENT DOCUMENTS

WO          92/12667         8/1992

OTHER PUBLICATIONS

International Search Report for PCT/FR2019/051778 mailed Sep. 11, 2019, 2 pages.
(Continued)

*Primary Examiner* — Brandi N Thomas
(74) *Attorney, Agent, or Firm* — NIXON & VANDERHYE

(57) ABSTRACT

Disclosed is a device including a detector producing a signal depending on variations of the pupil diameter of an eye of a subject, a display for presenting, to the subject, a light pattern subdivided into a plurality of regions, and an analyzer receiving the signal of the detector and analyzing the frequential content thereof. The display is controlled such that each region has a light intensity modulated at a respec-
(Continued)

tive modulation frequency, the modulation frequencies being different from one region to the next.

20 Claims, 2 Drawing Sheets

(58) Field of Classification Search
CPC ......... A61B 3/0041; A61B 3/111; A61B 3/14; A61B 5/16; A61B 3/103; A61B 5/1104; A61B 3/0025; A61B 3/102; A61B 3/1208; A61B 3/145; A61B 5/4088; A61B 5/6821; A61B 3/032; A61B 3/11; A61B 5/165; A61B 3/04; A61B 3/1173; A61B 3/12; A61B 3/135; A61B 3/152; A61B 3/18; A61B 5/0013; A61B 5/0077; A61B 5/4005; A61B 5/4082; A61B 5/7264; A61B 5/746; A61B 3/0083; A61B 3/10; A61B 3/1035; A61B 3/022; A61B 3/1015; A61B 3/1025; A61B 3/117; A61B 3/1176; A61B 3/1241; A61B 5/162; A61B 5/18; A61B 5/40; A61B 5/4845; G02B 2027/0178; G02B 27/017; G02B 27/00; G02B 27/0093; G02B 27/0172; G02B 30/27; G02B 30/33; G02B 2027/011; G02B 2027/0123; G02B 2027/0138; G02B 21/0012; G02B 26/00; G02B 26/06; G02B 27/01
See application file for complete search history.

(56) References Cited

OTHER PUBLICATIONS

Written Opinion of the ISA for PCT/FR2019/051778 mailed Sep. 11, 2019, 5 pages.

* cited by examiner

OCULAR OBSERVATION DEVICE

This application is the U.S. national phase of International Application No. PCT/FR2019/051778 filed Jul. 16, 2019 which designated the U.S. and claims priority to FR Patent Application No. 18 56737 filed Jul. 20, 2018, the entire contents of each of which are hereby incorporated by reference.

The present invention relates to techniques for observing the eyes of individuals, and more particularly to techniques intended to detect retinal diseases.

BACKGROUND

To obtain information on the state of a retina of an individual, either observations of the fundus, the retina being illuminated through the pupil and reflected light collected by a device such as an ophthalmoscope, or subjective tests, such as those based on the Amsler grid or the Humphrey visual field, are used.

Although these methods allow scotomas to be detected, or even located, they are not without drawbacks. Examination of the fundus takes a certain time, generally requires the pupil of the individual to be dilated, and may cause the individual discomfort. As for subjective tests, they rely on judgement calls by the practitioner and, therefore, are open to bias. If a subjective test is used to locate a scotoma on the retina, the person must be asked to detect targets (bright spots). Testing the entire retina may take a long time, typically more than 10-20 minutes.

There is therefore a need for a simple, rapid and objective technique for obtaining information on possible scotomas affecting an individual.

The invention meets this need.

SUMMARY

An eye observation device is thus provided, comprising:
a detector that produces a signal dependent on variations in the pupil diameter of an eye of a subject;
a display for presenting to the subject a luminous pattern that is subdivided into a plurality of regions, the display being controlled so that each region has a light intensity modulated at a respective modulation frequency, the modulation frequencies being different from one region to the next, the modulation frequencies being chosen so that none of them is a harmonic of another; and
an analyzer that receives the signal of the detector and that analyzes its frequency content.

The device may be used to implement an eye observation method intended to test the retina of a subject. This method comprises:
presenting to the subject a luminous pattern that is subdivided into a plurality of regions, each region having a light intensity modulated at a respective modulation frequency, the modulation frequencies being different from one region to the next;
detecting variations in pupil diameter of an eye of the subject;
transforming the variations in pupil diameter into a frequency domain, to obtain a transformed signal; and
analyzing the transformed signal at the modulation frequencies.

The test is based on the induction of periodic pupillary activities caused by sinusoidal, for example, luminance modulations that are distributed over the visual field. The task of the subject is simply to look at the center of the display for a relatively short period of time. If the response recorded by the detector and analyzed at a frequency associated with one of the regions is of relatively low level, this is an indication that the subject is likely to have a scotoma in a corresponding region of the retina.

In one embodiment, the regions of the luminous pattern are lower than or equal to 10 in number.

During the analysis of the frequency content of the signal of the detector by the analyzer, it is possible to effectively discriminate between the pupillary responses induced respectively by the light-intensity modulation of each region of the luminous pattern presented to the subject.

In one embodiment, the modulation frequencies are comprised between 0.1 and 10 Hz.

In one embodiment, the modulation frequencies are comprised between 0.5 and 5 Hz.

The test may be relatively rapid. Thus, the display may be controlled to present the luminous pattern to the subject and the analyzer may analyze the signal of the detector for a time shorter than two minutes.

In one embodiment, the regions of the luminous pattern comprise a first region located at the center of the pattern and second regions occupying angular sectors around the first region. The second regions of the luminous pattern may be distributed radially in a plurality of layers around the first region. Regarding the selection of the modulation frequencies assigned to the regions, the highest may be assigned to the first region in the center of the luminous pattern.

In one embodiment of the device, the analyzer is configured to take into account the power that a transform of the signal of the detector has in the frequency domain at the modulation frequencies. It may be configured to also take into account the phase that the transform of the signal has at the modulation frequencies.

BRIEF DESCRIPTION OF THE DRAWINGS

Other particularities and advantages of the present invention will become apparent from the following description of a non-limiting example of embodiment, which is given with reference to the appended drawings, in which.

DESCRIPTION OF EMBODIMENTS

Figure 1:
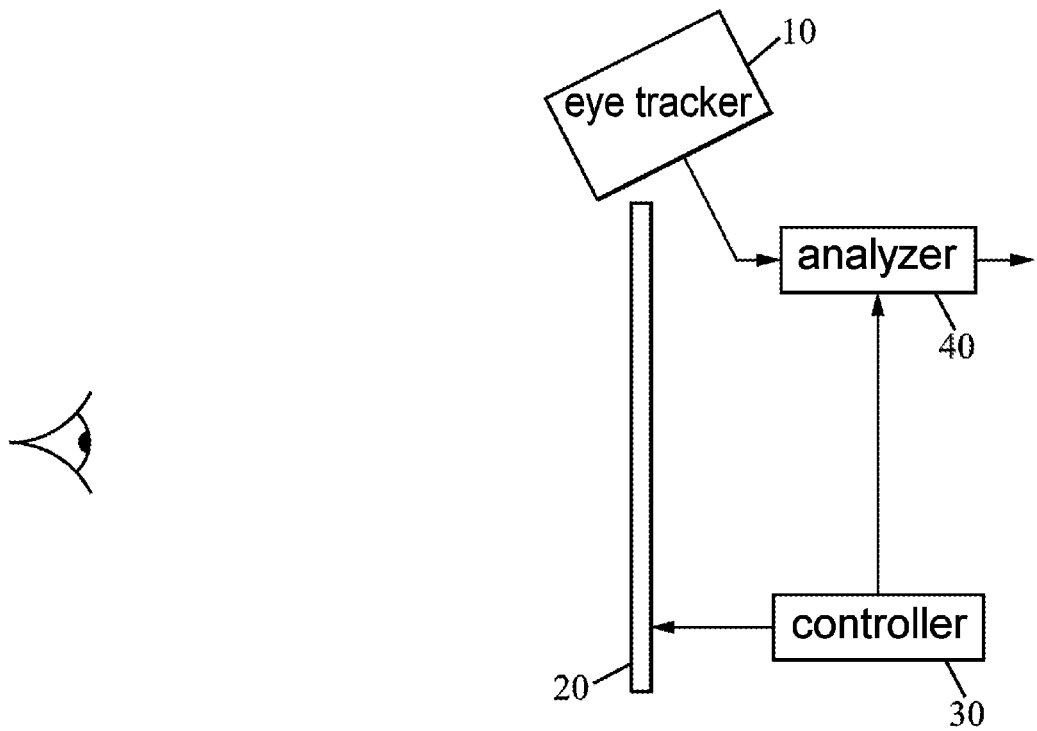
FIG. 1 is a schematic diagram of a device according to the invention.

With reference to FIG. 1, one embodiment of the device according to the invention comprises a detector 10, a display 20 controlled by a controller 30 and an analyzer 40.

The detector 10 is capable of providing information on variations in pupil diameter of a subject placed in front of the display 20. It may in particular be an eye tracker. An eye tracker (or oculometer) is an apparatus capable of measuring a certain number of parameters of an eye or the eyes of an individual, such as the position of the pupil of the right eye and/or the left eye, the pupil diameter of the right eye and/or the left eye, the direction of gaze, and/or the convergence and synchronism of the activities of the two eyes. In the application considered here, it will generally be possible to limit the information gathered to information on pupil diameter, which is recorded over time.

To make the measurements of the detector 10 more reliable, the device may also comprise a chin strap or another system for stabilizing the position of the head of the subject in front of the display 20.

The measurements on a subject using the device according to the invention are typically carried out eye by eye. It is preferable to mask the unmeasured eye.

The display 20 is for example a screen onto which a predefined luminous pattern is projected. It may also be a liquid-crystal or light-emitting-diode display. In another example, the detector 10 and the display 20 form part of a pupillometer.

The controller 30 controls the display 20 so that the latter presents, to the subject, a luminous pattern comprising a plurality of spatially distributed regions. In each region, the luminance of the pattern is modulated to exhibit a frequency-domain characteristic set by the controller 20. Each region may thus be associated with a respective modulation frequency. The subject is invited to direct their gaze toward a central point of the pattern.

The analyzer 40 receives the signal output from detector 10, which is dependent on the pupil diameter of the subject. It analyzes the frequency content of the signal in the band of the modulation frequencies employed in the luminous pattern. This analysis for example uses a Fourier transform of the time-domain variations in pupil diameter. Other time-frequency transforms may of course be used.

It is expected a priori that the Fourier spectrum thus computed will comprise a peak at each modulation frequency employed in the luminous pattern, because variable illumination of a segment of the retina normally engenders corresponding fluctuations in pupil diameter. However, if the retina has a scotoma, the peak will be weakened in the Fourier spectrum at the frequency associated with the region of the pattern that illuminates the scotomatous area.

It will be noted that pupil diameter reacts to the stimulus of the luminous pattern reflexively. The test performed using the device does not require any cognitive involvement on the part of the subject. It is an objective test. The subject is simply expected to focus on the center of the motif.

The time taken to carry out the test may be quite short, typically about one minute, this allowing the detector to record a number of luminance oscillations sufficient to make the Fourier-transform computation fine enough. A time shorter than two minutes has the advantage of stressing the subject for a short time only.

In the luminous pattern, the band of the modulation frequencies is chosen to reflect commonly observed physiological responses. The band is generally located in a range of 0.1 to 10 Hz, and typically in a range of 0.5 to 5 Hz.

Figure 2:
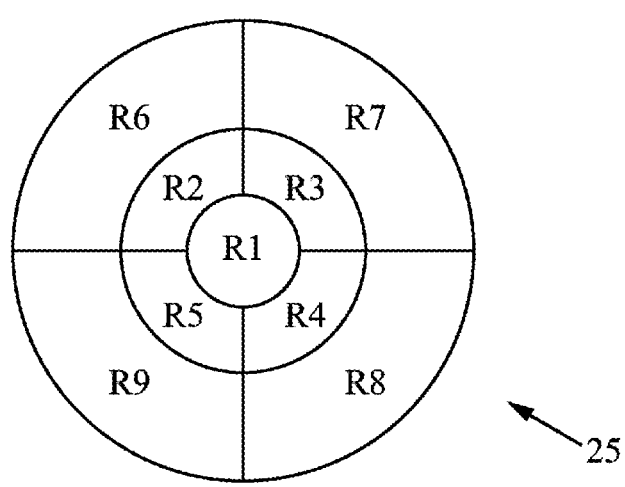
FIG. 2 is a diagram illustrating an example of a luminous pattern usable by a device according to the invention.

An example of the geometry of the luminous pattern displayed by display 20 is shown in FIG. 2. Here, the pattern comprises a central region R1 surrounded by peripheral regions R2-R9 that are distributed in two layers in the radial direction. The regions R2-R5 of the first radial layer occupy four angular sectors of 90° around the central region R1, while the regions R6-R9 of the second radial layer occupy four angular sectors of 90° around the regions R2-R5.

In one particular case, the luminance modulation frequencies employed in regions R1 to R9 are as follows:
region R1: modulation at 3.60 Hz;
region R2: modulation at 3.25 Hz;
region R3: modulation at 2.40 Hz;
region R4: modulation at 1.25 Hz;
region R5: modulation at 2.13 Hz;
region R6: modulation at 1.75 Hz;
region R7: modulation at 1.00 Hz;
region R8: modulation at 2.75 Hz;
region R9: modulation at 0.75 Hz.

It will be noted that among these nine modulation frequencies, the highest is the one associated with the central region R1 corresponding to the fovea. It is preferable for the frequencies to be selected so that, as in this example, one of them is not a harmonic of any other.

Figure 3:
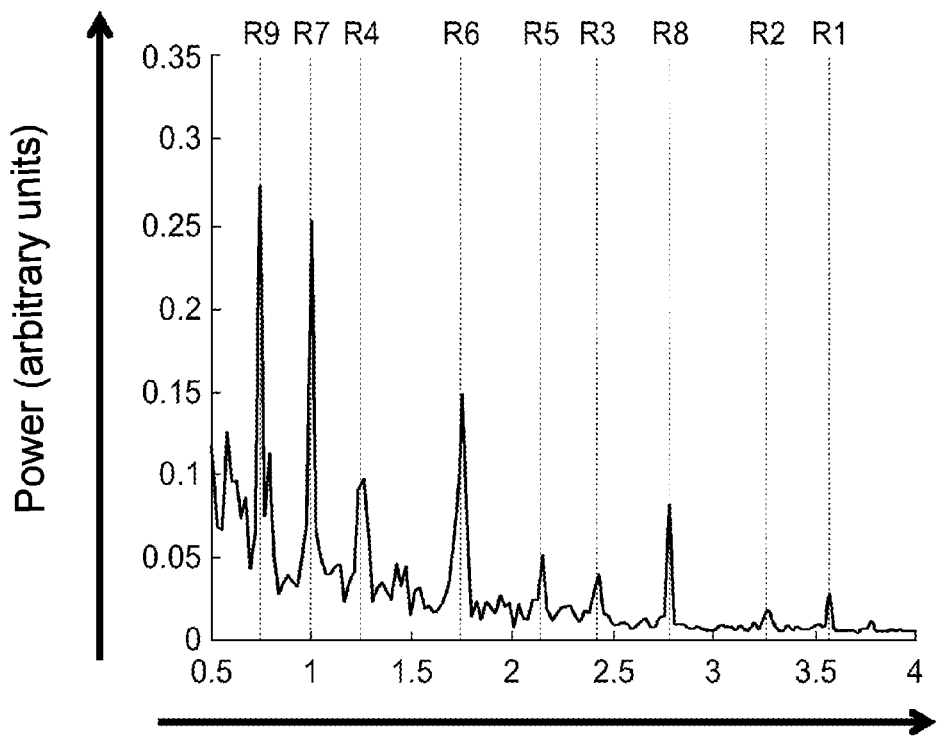
FIGS. 3 and 4 are graphs illustrating examples of Fourier analysis of the modulations of pupil diameter in a device according to the invention.

FIG. 3 illustrates results obtained on a healthy eye of an individual, showing, in arbitrary units, the modulus (power) $P_i$ of the discrete Fourier transform of the signal of the detector as a function of frequency i, as computed by the analyzer 40. As expected, therein a peak may be seen at the modulation frequency of each of the regions R1-R9. In the example shown, the modulation frequencies are such that none of them is a harmonic of another. Thus, the overlap between a first peak corresponding to the main modulation frequency of a first region and a second peak corresponding to a harmonic modulation frequency of a second region is avoided. Thus, each peak allows the pupillary response of the subject to the modulation of the luminance of a single given region of the luminous pattern to be qualified.

In addition, since the number of regions is lower than 10, each peak is clearly separated from adjacent peaks in the spectrum shown in FIG. 3. The pupillary response of the subject to the modulation of the luminance of each region of the luminous pattern may thus be quantified, for example on the basis of the height or of the integral of the peaks.

Figure 4:
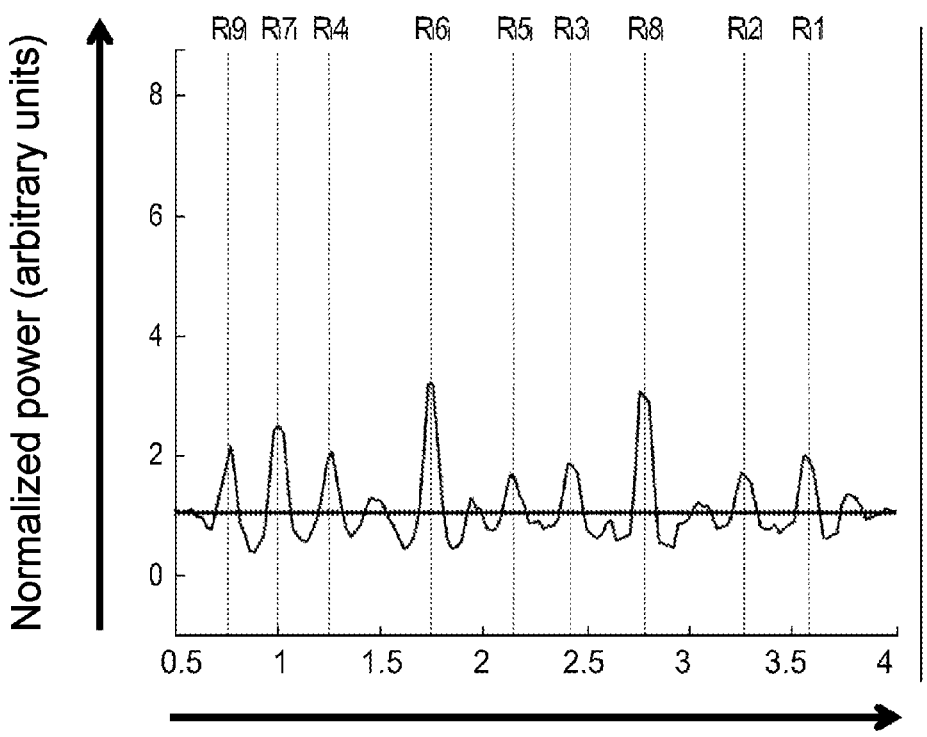

FIG. 4 is another representation of the results obtained for the same eye. Here, the power has been normalized to make it easier to view and compare the powers at the various modulation frequencies. Viewing is easier with this format. In this particular example, the technique used for the normalization consists in obtaining the normalized power $P'_i$ at a frequency i of the discrete spectrum by dividing the power in the vicinity of the frequency i by those of the frequencies of a broader neighborhood, according to the formula:

$$P'_i=(P_{i-1}+P_i+P_{i+1})/[(P_{i-4}+P_{i-3}+P_{i-2}+P_{i+2}+P_{i+3}+P_{i+4})/2]$$

Other normalization methods may be used, provided that they meet the normalization objective, i.e. make inter-frequency comparisons of the stimulated powers possible.

If an eye of a subject has a scotoma, at least one of the power peaks visible at the frequencies R1-R9 is decreased. The frequency at which the decrease is observed provides information on the location of the scotoma on the retina.

Phase information, representing the delay between the variation in luminance and the pupillary response may be used to refine the results obtained by analyzing power $P_i$ or $P'_i$.

The phase of the Fourier transform of the signal of the detector depends on the delay between the stimulation and the pupillary response, and therefore is a complementary variable allowing a scotoma to be detected. Specifically, a poor transmission of the retinal signal is expected to result in a larger phase shift in the response. By associating the regions R1-R9 with different modulation (stimulation) frequencies, it is possible to identify regions that respond with an abnormal phase shift, indicative of a probable scotoma. A mixed variable, combining power and phase shift at modulation frequencies, is therefore apt to provide a better sensitivity with respect to detection of deficient areas of the retina.

The advantages of the frequency-domain pupil test performed using the device presented above include:
absence of a subjective task;
rapidity;

objective measurement related to measurement of the pupil;

ability to locate the defect on the retina.

This test is especially applicable to the screening and diagnosis of ophthalmological diseases (macular degeneration, glaucoma, etc.).

The embodiments described above are a simple illustration of the present invention. Various modifications may be made to them without departing from the scope of the appended claims.

The invention claimed is:

1. An eye observation device, comprising:
    a detector that produces a signal dependent on variations in the pupil diameter of an eye of a subject;
    a display configured to present to the subject a luminous pattern that is subdivided into a plurality of regions, the display being controlled so that each of the regions has a light intensity periodically modulated at a respective modulation frequency, the modulation frequencies being different from one region to the next, the modulation frequencies being chosen so that none of the modulation frequencies is a harmonic of another; and
    an analyzer that receives the signal of the detector and that analyzes a frequency content of the signal.

2. The device as claimed in claim 1, wherein the modulation frequencies are comprised between 0.1 and 10 Hz.

3. The device as claimed in claim 2,
    wherein the modulation frequencies are comprised between 0.5 and 5 Hz.

4. The device as claimed in claim 1, wherein the regions of the luminous pattern are lower than or equal to 10 in number.

5. The device as claimed in claim 1, wherein the display is controlled to present the luminous pattern to the subject for a time shorter than two minutes and the analyzer analyzes the signal of the detector for said time.

6. The device as claimed in claim 1, wherein the regions of the luminous pattern comprise a first region located in the center of the pattern and second regions occupying angular sectors around the first region.

7. The device as claimed in claim 6, wherein the second regions of the luminous pattern are distributed radially in a plurality of layers around the first region.

8. The device as claimed in claim 6, wherein the modulation frequency is higher in the first region than in the second regions of the luminous pattern.

9. The device as claimed in claim 1, wherein the analyzer is configured to take into account the power that a transform of the signal of the detector has in the frequency domain at the modulation frequencies.

10. The device as claimed in claim 9, wherein the analyzer is configured to further take into account the phase that the transform of the signal of the detector has at the modulation frequencies.

11. The device as claimed in claim 2, wherein the regions of the luminous pattern are lower than or equal to 10 in number.

12. The device as claimed in claim 3, wherein the regions of the luminous pattern are lower than or equal to 10 in number.

13. The device as claimed in claim 2, wherein the display is controlled to present the luminous pattern to the subject for a time shorter than two minutes and the analyzer analyzes the signal of the detector for said time.

14. The device as claimed in claim 3, wherein the display is controlled to present the luminous pattern to the subject for a time shorter than two minutes and the analyzer analyzes the signal of the detector for said time.

15. The device as claimed in claim 4, wherein the display is controlled to present the luminous pattern to the subject for a time shorter than two minutes and the analyzer analyzes the signal of the detector for said time.

16. The device as claimed in claim 2, wherein the regions of the luminous pattern comprise a first region located in the center of the pattern and second regions occupying angular sectors around the first region.

17. The device as claimed in claim 3, wherein the regions of the luminous pattern comprise a first region located in the center of the pattern and second regions occupying angular sectors around the first region.

18. The device as claimed in claim 4, wherein the regions of the luminous pattern comprise a first region located in the center of the pattern and second regions occupying angular sectors around the first region.

19. The device as claimed in claim 5, wherein the regions of the luminous pattern comprise a first region located in the center of the pattern and second regions occupying angular sectors around the first region.

20. The device as claimed in claim 7, wherein the modulation frequency is higher in the first region than in the second regions of the luminous pattern.

* * * * *